(12) United States Patent
DeSalvo (10) Patent No.: US 8,932,264 B2
(45) Date of Patent: Jan. 13, 2015

(54) MEDICATION DELIVERY PEN ASSEMBLY WITH NEEDLE LOCKING SAFETY SHIELD

(75) Inventor: David E. DeSalvo, Butler, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1729 days.

(21) Appl. No.: 10/638,729

(22) Filed: Aug. 11, 2003

(65) Prior Publication Data

US 2005/0038392 A1    Feb. 17, 2005

(51) Int. Cl.
*A61M 5/00* (2006.01)
*A61M 5/32* (2006.01)

(52) U.S. Cl.
CPC ..... *A61M 5/3243* (2013.01); *A61M 2005/3247* (2013.01)
USPC .......................................... 604/187; 604/110

(58) Field of Classification Search
CPC ..... A61M 5/002; A61M 5/24; A61M 5/3202; A61M 5/30; A61M 5/31533
USPC ........... 604/110, 192–198, 187, 164.08, 207, 604/208, 218, 221, 222, 228, 229, 240, 604/164.12
See application file for complete search history.

(56) References Cited

U.S. PATENT DOCUMENTS

| | | | |
|---|---|---|---|
| 2,752,918 A | 7/1956 | Uytenbogaart | |
| 3,712,301 A | 1/1973 | Sarnoff | |
| 3,882,863 A | 5/1975 | Sarnoff et al. | |
| 4,031,893 A | 6/1977 | Kaplan et al. | |
| 4,214,584 A | 7/1980 | Smirnov et al. | |
| 4,226,235 A | 10/1980 | Sarnoff et al. | |
| 4,373,526 A * | 2/1983 | Kling | 604/117 |
| 4,413,760 A | 11/1983 | Paton | |
| 4,565,543 A | 1/1986 | Bekkering et al. | |
| 4,624,660 A | 11/1986 | Mijers et al. | |
| 4,755,169 A | 7/1988 | Sarnoff et al. | |
| 4,804,372 A * | 2/1989 | Laico et al. | 604/198 |

(Continued)

FOREIGN PATENT DOCUMENTS

EP    0 586 199 A1    9/1994
JP    H 8-276012 A    10/1996

(Continued)

*Primary Examiner* — Kevin C Sirmons
*Assistant Examiner* — Phillip Gray
(74) *Attorney, Agent, or Firm* — Alan W. Fiedler; Fitzpatrick, Cella, Harper & Scinto (57) ABSTRACT

A medication delivery pen assembly having a pen body and a needle assembly with a hub connected to the pen body, a needle cannula extending through the hub with a distal end sharpened for insertion into a patient, and a shield having a tubular portion telescopingly disposed about at least a portion of the hub. The tubular portion includes an internal surface, at least one projection extending inwardly from the internal surface, and the hub having at least one externally extending projection. The shield is axially displaceable relatively along the hub distally from a first position, where the distal end of the needle cannula is exposed, to a second position, where the distal end of the needle cannula is enclosed by the shield. Upon the shield being displaced to the second position, the at least one projection on the hub is deflectibly urged passed the at least one projection on the tubular portion so that subsequent distal-to-proximal movement of the shield relative to the hub is hindered by interengagement of the projections. The needle cannula may be directly affixed to the pen body with the hub being formed unitarily with, rigidly affixed to, or removably affixed to the pen body.

19 Claims, 4 Drawing Sheets

(56) References Cited

U.S. PATENT DOCUMENTS

| | | | |
|---|---|---|---|
| 4,822,340 A | 4/1989 | Kamstra | |
| 4,826,490 A | 5/1989 | Byrne et al. | |
| 4,921,491 A | 5/1990 | Champ | |
| 4,947,863 A * | 8/1990 | Haber et al. | 604/110 |
| 4,968,302 A | 11/1990 | Schluter et al. | |
| 5,017,190 A | 5/1991 | Simon et al. | |
| 5,066,277 A * | 11/1991 | Carrell et al. | 604/110 |
| 5,085,641 A | 2/1992 | Sarnoff et al. | |
| 5,085,642 A | 2/1992 | Sarnoff et al. | |
| 5,104,380 A | 4/1992 | Holman et al. | |
| 5,112,317 A | 5/1992 | Michel | |
| 5,169,392 A | 12/1992 | Ranford et al. | |
| 5,201,721 A | 4/1993 | Lee et al. | |
| 5,226,895 A | 7/1993 | Harris | |
| 5,226,896 A | 7/1993 | Harris | |
| 5,244,465 A | 9/1993 | Michel | |
| 5,279,585 A | 1/1994 | Balkwill | |
| 5,279,586 A | 1/1994 | Balkwill | |
| 5,295,975 A * | 3/1994 | Lockwood, Jr. | 604/198 |
| 5,295,976 A | 3/1994 | Harris | |
| 5,300,030 A | 4/1994 | Crossman et al. | |
| 5,304,152 A | 4/1994 | Sams | |
| 5,312,347 A * | 5/1994 | Osborne et al. | 604/110 |
| D347,894 S | 6/1994 | Hansen et al. | |
| 5,328,485 A * | 7/1994 | Moreno et al. | 604/198 |
| 5,330,426 A | 7/1994 | Kriesel et al. | |
| 5,342,309 A * | 8/1994 | Hausser | 604/110 |
| 5,358,489 A | 10/1994 | Wyrick | |
| 5,383,865 A | 1/1995 | Michel | |
| 5,391,151 A | 2/1995 | Wilmot | |
| 5,415,645 A | 5/1995 | Friend et al. | |
| 5,417,660 A | 5/1995 | Martin | |
| 5,417,662 A | 5/1995 | Hjertman et al. | |
| 5,429,612 A | 7/1995 | Berthier | |
| 5,437,639 A * | 8/1995 | Malenchek | 604/110 |
| 5,478,316 A | 12/1995 | Bitdinger et al. | |
| 5,480,387 A | 1/1996 | Gabriel et al. | |
| 5,514,097 A | 5/1996 | Knauer | |
| 5,540,664 A | 7/1996 | Wyrick | |
| 5,545,145 A | 8/1996 | Clinton et al. | |
| 5,549,558 A | 8/1996 | Martin | |
| 5,569,192 A | 10/1996 | van der Wal | |
| 5,584,815 A | 12/1996 | Pawelka et al. | |
| 5,593,390 A | 1/1997 | Castellano et al. | |
| 5,595,566 A | 1/1997 | Vallelunga | |
| 5,620,421 A | 4/1997 | Schmitz | |
| 5,626,566 A | 5/1997 | Petersen et al. | |
| 5,634,910 A | 6/1997 | Kanner et al. | |
| 5,637,094 A | 6/1997 | Stewart, Jr. et al. | |
| 5,645,534 A | 7/1997 | Chanoch | |
| 5,658,254 A | 8/1997 | Reichenbach et al. | |
| 5,658,259 A | 8/1997 | Pearson et al. | |
| 5,665,071 A | 9/1997 | Wyrick | |
| 5,679,111 A | 10/1997 | Hjertman et al. | |
| 5,688,251 A | 11/1997 | Chanoch | |
| 5,693,027 A | 12/1997 | Hansen et al. | |
| 5,695,472 A | 12/1997 | Wyrick | |
| 5,709,662 A | 1/1998 | Olive et al. | |
| 5,725,508 A | 3/1998 | Chanoch et al. | |
| 5,728,074 A | 3/1998 | Castellano et al. | |
| 5,746,727 A | 5/1998 | Graves et al. | |
| 5,779,683 A | 7/1998 | Meyer | |
| 5,820,602 A | 10/1998 | Kovelman et al. | |
| 5,827,232 A | 10/1998 | Chanoch et al. | |
| 5,829,589 A | 11/1998 | Nguyen et al. | |
| 5,836,911 A | 11/1998 | Marzynski et al. | |
| 5,843,036 A | 12/1998 | Olive et al. | |
| 5,873,462 A | 2/1999 | Nguyen et al. | |
| 5,873,856 A | 2/1999 | Hjertman et al. | |
| 5,893,845 A | 4/1999 | Newby et al. | |
| 5,928,205 A | 7/1999 | Marshall | |
| 5,938,642 A | 8/1999 | Burroughs et al. | |
| 5,941,857 A | 8/1999 | Nguyen et al. | |
| 5,944,700 A | 8/1999 | Nguyen et al. | |
| 5,951,530 A | 9/1999 | Steengaard et al. | |
| 5,957,896 A | 9/1999 | Bendek et al. | |
| 5,961,495 A | 10/1999 | Walters et al. | |
| 5,964,731 A | 10/1999 | Kovelman | |
| 5,964,739 A | 10/1999 | Champ | |
| 5,968,021 A | 10/1999 | Ejlersen | |
| 5,971,966 A | 10/1999 | Lav | |
| 5,980,491 A | 11/1999 | Hansen | |
| 5,984,900 A | 11/1999 | Mikkelsen | |
| 5,984,906 A | 11/1999 | Bonnichsen et al. | |
| RE36,447 E | 12/1999 | Byrne et al. | |
| 6,001,082 A | 12/1999 | Dair et al. | |
| 6,001,089 A | 12/1999 | Burroughs et al. | |
| 6,004,297 A | 12/1999 | Steenfeldt-Jensen et al. | |
| 6,017,329 A | 1/2000 | Hake | |
| 6,039,713 A | 3/2000 | Botich et al. | |
| 6,048,336 A | 4/2000 | Gabriel | |
| 6,056,728 A | 5/2000 | von Schuckmann | |
| 6,077,247 A | 6/2000 | Marshall et al. | |
| 6,077,253 A | 6/2000 | Cosme | |
| 6,090,080 A | 7/2000 | Jost et al. | |
| 6,093,172 A | 7/2000 | Funderburk et al. | |
| 6,110,149 A | 8/2000 | Klitgaard et al. | |
| 6,126,646 A | 10/2000 | Hansen et al. | |
| 6,159,181 A | 12/2000 | Crossman et al. | |
| 6,193,698 B1 | 2/2001 | Kirchhofer et al. | |
| 6,203,529 B1 * | 3/2001 | Gabriel et al. | 604/192 |
| 6,221,046 B1 | 4/2001 | Burroughs et al. | |
| 6,221,053 B1 | 4/2001 | Walters et al. | |
| 6,241,709 B1 | 6/2001 | Bechtold et al. | |
| 6,248,095 B1 | 6/2001 | Giambattista et al. | |
| 6,277,097 B1 | 8/2001 | Mikkelsen et al. | |
| 6,277,099 B1 | 8/2001 | Strowe et al. | |
| 6,277,101 B1 | 8/2001 | Kirchhofer et al. | |
| 6,319,225 B1 | 11/2001 | Sugita et al. | |
| 6,391,003 B1 * | 5/2002 | Lesch, Jr. | 604/110 |
| 6,429,612 B1 | 8/2002 | Kume et al. | |
| 6,776,776 B2 * | 8/2004 | Alchas et al. | 604/198 |
| 6,790,199 B1 * | 9/2004 | Gianakos | 604/197 |
| 6,796,967 B2 * | 9/2004 | Jensen | 604/197 |
| 6,843,781 B2 * | 1/2005 | Alchas et al. | 604/117 |
| 6,855,129 B2 * | 2/2005 | Jensen et al. | 604/110 |
| 7,074,211 B1 * | 7/2006 | Heiniger et al. | 604/198 |
| 7,083,599 B2 * | 8/2006 | Alchas et al. | 604/198 |
| 7,108,679 B2 * | 9/2006 | Alchas | 604/117 |
| 7,241,275 B2 * | 7/2007 | Alchas et al. | 604/117 |
| 2001/0005781 A1 | 6/2001 | Bergens et al. | |
| 2001/0009990 A1 | 7/2001 | Hostettler et al. | |
| 2001/0020155 A1 | 9/2001 | Mikkelsen et al. | |
| 2001/0051792 A1 | 12/2001 | Kirchhofer et al. | |
| 2002/0004648 A1 | 1/2002 | Larsen et al. | |
| 2002/0133122 A1 | 9/2002 | Giambattista et al. | |
| 2003/0120209 A1 | 6/2003 | Jensen et al. | |

FOREIGN PATENT DOCUMENTS

| | | |
|---|---|---|
| WO | WO 92/19296 | 11/1992 |
| WO | WO 97/14455 | 4/1997 |
| WO | WO 01/91837 A1 | 12/2001 |
| WO | WO 02/09797 | 2/2002 |

* cited by examiner

MEDICATION DELIVERY PEN ASSEMBLY WITH NEEDLE LOCKING SAFETY SHIELD

BACKGROUND OF THE INVENTION

This invention relates to needle safety devices for medication delivery pens, and more particularly, to manually-actuated safety devices for medication delivery pens.

Medication delivery pens are known in the art and are used extensively for self-administered injections, particularly with insulin. Although a medication delivery pen is normally only handled by its user, concerns exist with inadvertent skin penetration by a used pen injection needle (also referred to as a "needle stick") particularly after disposal of a used needle.

Devices have been developed in the prior art for shielding a used medication delivery pen needle. Generally, prior art devices require complex parts and/or a multiplicity of parts. As a result, these prior art devices may not only be expensive, but may also be susceptible to failure due to their complexity. For example, U.S. Pat. No. 5,964,731, which issued on Oct. 12, 1999, discloses a manually-actuatable needle cover which includes a needle cover that is rotated through a helical track into a locked shielding position. This device, however, requires both the shielding element and an outer collar which includes the helical track. In an alternative design, as disclosed in U.S. Published patent application Ser. No. US 2002/0133122 A1, which published on Sep. 19, 2002, a normally-biased-closed shield is disclosed which is retracted upon pressing engagement against the skin of a patient. After administration, the shield locks in a protective position about the used needle. Although this device provides passive shielding without patient involvement, patients have no or poor visual contact of the needle cannula end to observe priming of the needle before use (priming of the needle is typically recommended with a small amount of liquid being expelled from the needle prior to injection to ensure that no air bubbles are entrapped within the needle).

SUMMARY OF THE INVENTION

To overcome shortcomings of the prior art, in one aspect of the subject invention, a medication delivery pen assembly is provided having a pen body and a needle assembly with a hub connected to the pen body, a needle cannula extending through the hub with a distal end sharpened for insertion into a patient, and a shield having a tubular portion telescopingly disposed about at least a portion of the hub. The tubular portion includes an internal surface, at least one projection extending inwardly from the internal surface, and the hub having at least one externally extending projection. The shield is axially displaceable relatively along the hub distally from a first position, where the distal end of the needle cannula is exposed, to a second position, where the distal end of the needle cannula is enclosed by the shield. Upon the shield being displaced to the second position, the at least one projection on the hub is deflectibly urged passed the at least one projection on the tubular portion so that subsequent distal-to-proximal movement of the shield relative to the hub is hindered by interengagement of the projections.

The subject invention is also directed to a needle assembly having a hub, a needle cannula extending through the hub with a distal end sharpened for insertion into a patient, and a shield having a tubular portion telescopingly disposed about at least a portion of the hub. The tubular portion includes an internal surface, at least one projection extending inwardly from the internal surface, and the hub having at least one externally extending projection. The shield is axially displaceable relatively along the hub distally from a first position, where the distal end of the needle cannula is exposed, to a second position, where the distal end of the needle cannula is enclosed by the shield. Upon the shield being displaced to the second position, the at least one projection on the hub is deflectibly urged passed the at least one projection on the tubular portion so that distal-to-proximal movement of the shield relative to the hub is hindered by interengagement of the projections.

The subject invention is further directed to a medication delivery pen assembly having a pen body with a needle cannula affixed thereto, the needle cannula having a distal end sharpened for insertion into a patient, a hub disposed about a portion of the needle cannula, and a shield having a tubular portion telescopingly disposed about at least a portion of the hub. The tubular portion includes an internal surface, at least one projection extending inwardly from the internal surface, and the hub having at least one externally extending projection. The shield is axially displaceable relatively along the hub distally from a first position, where the distal end of the needle cannula is exposed, to a second position, where the distal end of the needle cannula is enclosed by the shield. Upon the shield being displaced to the second position, the at least one projection on the hub is urged passed the at least one projection on the tubular portion so that distal-to-proximal movement of the shield relative to the hub is hindered by interengagement of the projections.

With the subject invention, a manually-actuatable shield is provided which is axially displaceable and that advantageously locks into a safety position enclosing a used needle. The needle assembly is preferably removable from the pen body so as to allow for needle changes, as required. The shield remains in its safety position on the needle assembly after removal and/or after disposal of the entire assembly and minimizes the chances of needle sticks occurring. As will be recognized by those skilled in the art, the subject invention can also be used in embodiments where the needle cannula is fixed to the pen body. Here, the hub can be formed unitarily with, rigidly affixed to, or removably affixed to the pen body.

As used herein, the term "proximal" and derivatives thereof, shall mean the end of an item or direction away from a patient during use of the subject invention. The term "distal", and derivatives thereof, shall mean the end of an item or direction towards a patient during use of the subject invention.

These and other features of the invention will be better understood through a study of the following detailed description and accompanying drawings.

DETAILED DESCRIPTION OF THE INVENTION

Figure 1:
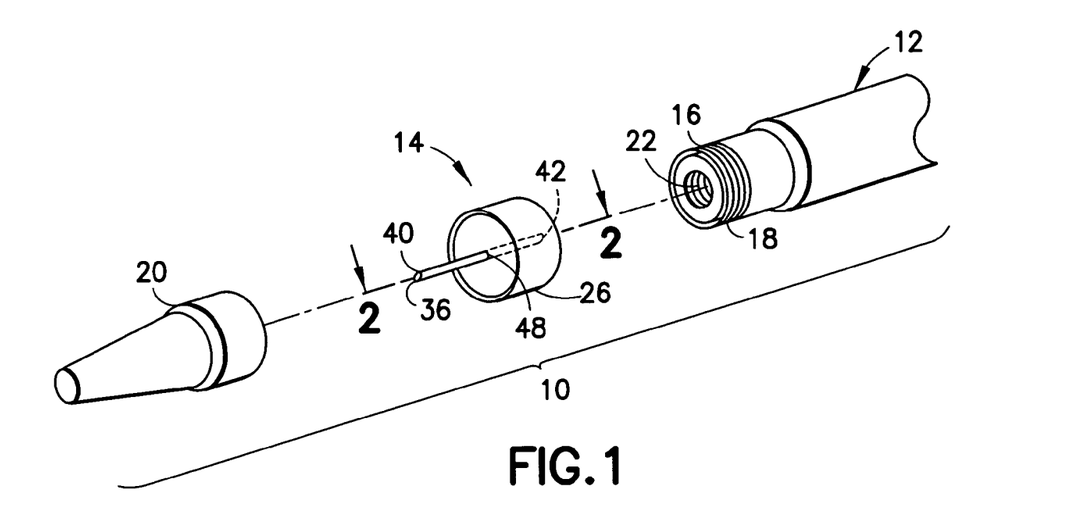
FIG. 1 is a partial exploded view of a medication delivery pen and needle assembly formed in accordance with the subject invention.

With reference to FIG. 1, a medication delivery pen assembly 10 is provided which generally includes a pen body 12 and a needle assembly 14. The pen body 12 may be of any type, including that disclosed in U.S. Pat. No. 6,248,095 B1, which issued on Jun. 19, 2001, to the assignee herein. The disclosure of U.S. Pat. No. 6,248,095 B1 is incorporated herein by reference.

The pen body 12 includes a distal end 16 onto which the needle assembly 14 is removably mounted using any known technique, including threaded connections and slip connections. By way of non-limiting example, threads 18 are shown about the pen body 12 at the distal end 16. Preferably, the needle assembly 14 is detachably mounted onto the pen body 12 to allow for removal therefrom after use, although the needle assembly 14 may be non-removably affixed to the distal end 16 where the assembly 10 does not require needle assembly replacement, such as with a single-dose unit. Optionally, a cap 20 may be provided which is formed to releasably mount onto the pen body 12, such as with a snap or interference fit, to limit contamination of the needle assembly 14 and/or aperture 22 defined in distal end 16 of pen body 12 and which provides access into the interior of the pen body 12. The cap may be formed in the same manner as the cap disclosed in U.S. Published patent application Ser. No. 2002/0133122 A1. U.S. Published patent application Ser. No. 2002/0133122 A1 is incorporated by reference herein in its entirety.

Figure 2:
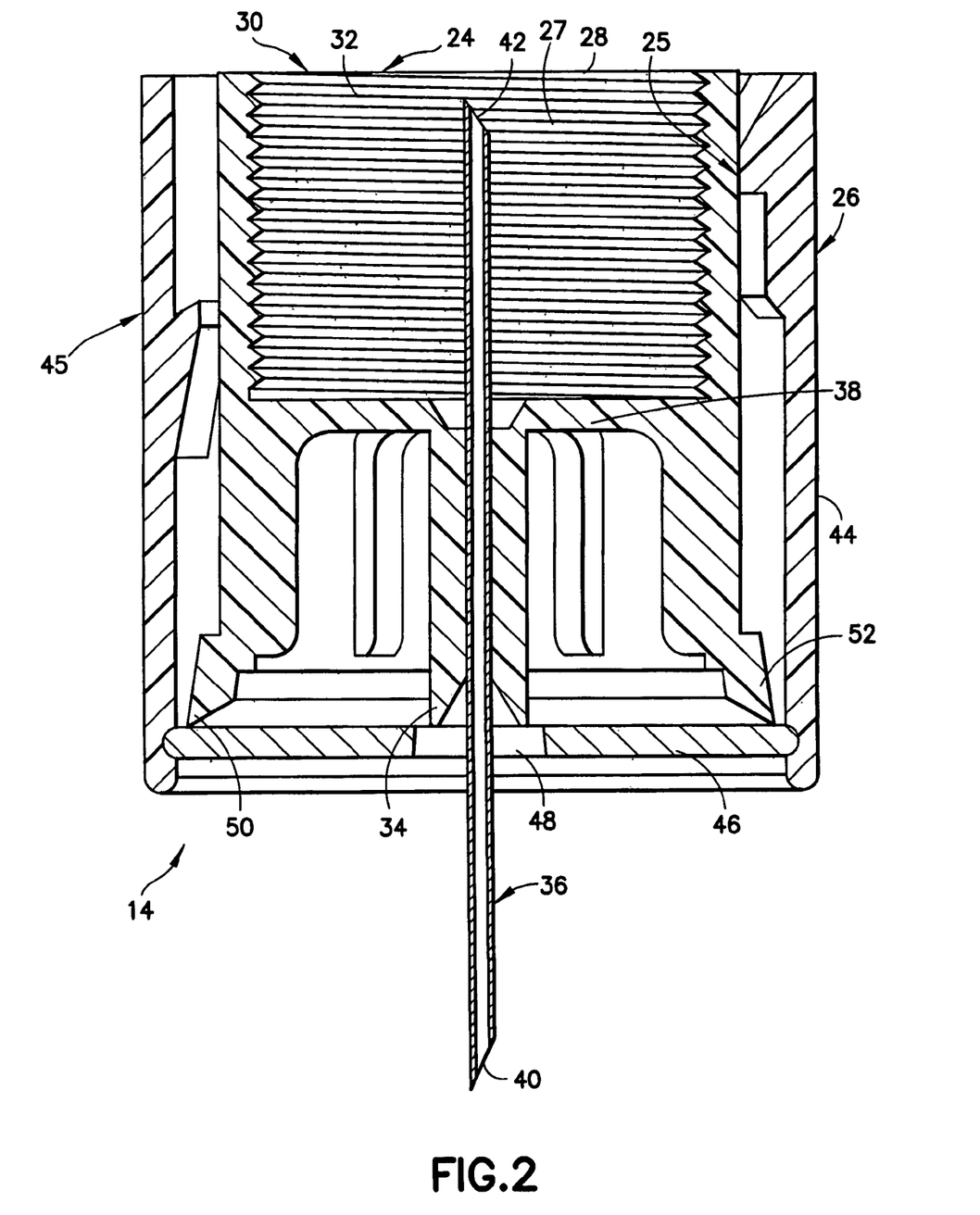
FIG. 2 is a cross-sectional view of a needle assembly taken along line of 2-2 of FIG. 1 with the shield in a retracted position and with the needle cannula exposed.

In a first embodiment of the subject invention, the needle assembly 14 is formed separate from the pen body 12. As more clearly shown in FIG. 2, the needle assembly 14 includes a hub 24 with a needle shield 26 at least partially telescopingly disposed about the hub 24. The hub 24 defines a cavity 27 with a wall 28 having a proximal end 30; the cavity 27, wall 28 and proximal end 30 being sized and shaped, and the wall 28 having feature(s) defined thereon, for mounting onto the distal end 16 of the pen body 12. For example, as shown in FIG. 2, thread members 32 may be formed on an interior of the wall 28 for threaded mounting onto the threads 18 defined on pen body 12. A needle mounting member 34 is also provided which rigidly holds a needle cannula 36, such as, for example, with an interference fit. The needle cannula 36 may be affixed to the needle mounting member 34 using any known technique, such as with adhesive. Transverse webbing 38 connects the wall 28 and the needle mounting member 34.

The needle cannula 36 may be of any known design and includes a sharpened distal end 40 for insertion into a patient. Preferably, proximal end 42 of the needle cannula 36 facilitates insertion into a septum of a medicinal container (not shown) that may be located inside the pen body 12; the septum being located adjacent the aperture 22.

The shield 26 includes a generally tubular portion 44. In an initial state, as shown in FIG. 2, the tubular portion 44 is generally coextensive with the hub 24 and the needle cannula 36 is exposed. Preferably, a cover 46 may be provided in proximity to a distal end of the shield 26 which includes an aperture 48 formed for the passage therethrough of the needle cannula 36. The cover 46 may prevent or restrict undesired proximal movement of the shield 26. It is preferred that the cover 46 be formed integrally with the tubular portion 44. By interengaging with the hub 24, the cover 46 advantageously prevents the shield 26 from moving excessively proximally relative to the hub 24 with the shield being in its initial state as shown in FIG. 2. If the cover 46 is not provided, one or more stop members may be provided to extend inwardly from the shield 26 to engage a distal end 50 of the hub 24 and, thus, restrict proximal movement of the shield 26 relative to the hub 24. It is also preferred that the hub 24 and the shield 26 be releasably engaged in the initial state, such as by forming a slight interference or detent fit between the two elements which may be manually overcome in displacing the shield 26 distally as described below. This limited engagement is intended to prevent inadvertent distal movement of the shield 26. For example, distal end 50 of the hub 24 may be formed with one or more outwardly flared portions 52 which interferingly engage with the interior of the tubular portion 44. It is preferred (but not required) that the flared portions 52 be continuous about the hub 24 in an annular shape. Alternatively, or in addition to, one or more engagement surfaces 25 may extend inwardly from the tubular portion 44 for interferingly engaging the hub 24 at its proximal end. It will be apparent from the disclosure provided herein that other structure on the hub 24 and/or shield 26 may provide the desired interference to prevent or restrict undesired movement of the shield 26 from the first position (depicted in FIG. 2).

Figure 3:
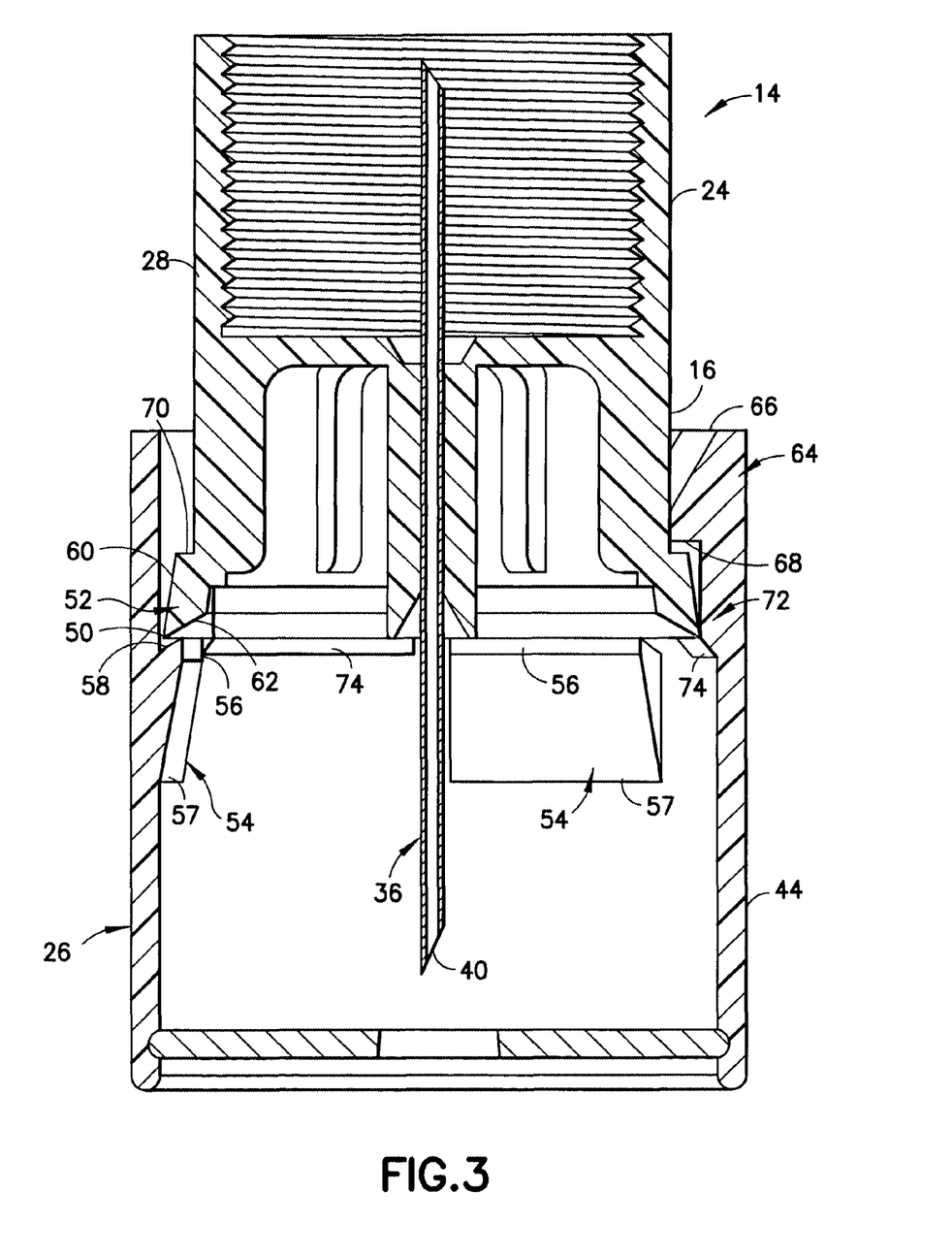
FIG. 3 is a cross-sectional view of the needle assembly shown in FIG. 2 with the shield in an extended position and with the needle cannula enclosed by the shield.
Figure 4:
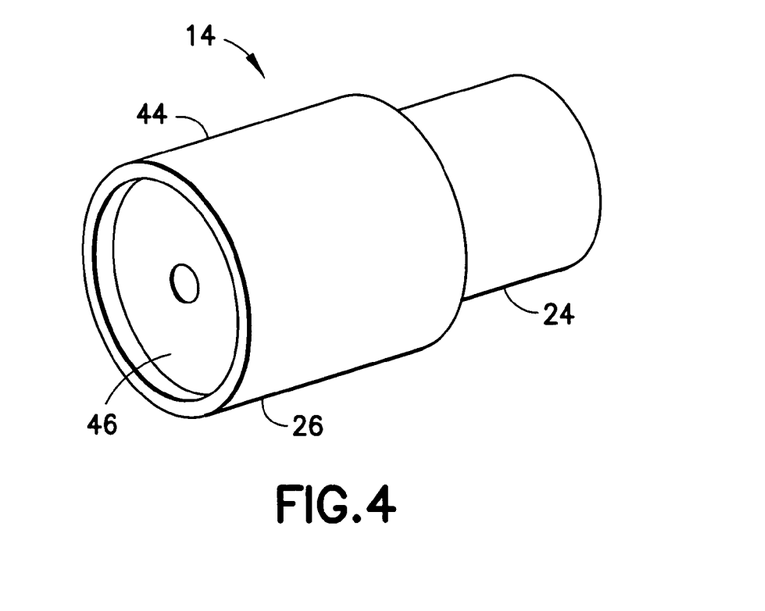
FIG. 4 is a perspective view of the needle assembly shown in FIG. 3.

The shield 26 is axially displaceable relative to the hub 24, and FIGS. 3 and 4 show the shield 26 being in an extended position relative to the hub 24 so as to enclose the distal end 40 of the needle cannula 36. The tubular portion 44 has an external surface 45 which is unobstructed so as to be engagable by a user to cause relative movement between the hub 24 and the shield 26. The external surface 45 of the tubular portion 44 may be textured or include reliefs or cut-outs to enhance the ability of a user to firmly grip and handle the shield 26. To provide holding force to the shield 26 in the first position, it is preferred, although not required, that the flared portions 52 be formed to have an outer diameter slightly greater than the internal diameter of the shield 26 (i.e., to form an interference fit). With the hub 24 and the shield 26 being formed of a resilient material, such as thermoplastic, the flared portions 52 thus formed may resiliently press against the shield 26 and releasably hold it in the first position.

It is also preferred that the shield 26 be lockable in the extended position shown in FIGS. 3 and 4. As will be appreciated by those skilled in the art and from the disclosure provided herein, various locking mechanisms can be used. For illustrative purposes, an exemplary arrangement is depicted. One or more projections 54 extend inwardly from the interior of the shield 26, preferably being ramped with inclined surfaces 56 that face distally and inwardly. Preferably, the projections 54 are circumferentially spaced-apart on the interior of the shield 26. Each projection 54 has an upper surface 58 preferably disposed at an acute angle relative to the respective inclined surface 56 (i.e., an acute angle is subtended between the upper surface 58 and the inclined surface 56). It is further preferred that the upper surfaces 58 not incline inwardly, but rather outwardly (i.e., the upper surfaces 58 preferably face proximally and outwardly, not proximally and inwardly). It is also further preferred that the upper surfaces 58 be aligned so as to collectively define a shelf (continuous or interrupted). Secondary inclined surfaces 57 may also be provided that define a greater taper leading to the inclined surfaces 56. As such, the secondary inclined surfaces 57 allow for the projections 54 to have shorter lengths (distal to proximal) than if the inclined surfaces 56 extended directly to the tubular portion 44.

Preferably, the flared portions 52 of the hub 24 have first and second inclined surfaces 60 and 62 that converge at the distal end 50 of the hub 24. The first inclined surface 60 faces proximally and outwardly, while the second inclined surface 62 faces distally and inwardly. Upon displacing the shield 26 distally from its initial position to the extended position, the flared portions 52 are deflectably urged past the projections 54 formed on the shield 26. The ramped configurations of the projections 54 and the flared portions 52 facilitate the deflection of the flared portions 52 with the first inclined surfaces 60 of the flared portions 52 riding over the inclined surfaces 56 (and secondary inclined surfaces 57, if used) of the projections 54. The distal end 50 is formed with a larger inner diameter than that defined between the projections 54 and, thus, once the shield 26 is in the second position (depicted in FIG. 3), movement of the shield 26 from the second position to the first position is hindered by interengagement of the flared portions 52 and the projections 54. Additionally, the upper surfaces 58 of the projections 54 coact with the second inclined surfaces 62 of the flared portions 52 to further hinder distal-to-proximal movement with the shield 26 being in the extended position. In particular, because of the convergent shape of the distal end 50, the distal end 50 will ride down the upper surfaces 58 upon being proximately urged; consequently, the distal end 50 will expand into a slightly enlarged state in which it is even more difficult to by-pass the projections 54 than with the distal end 50 being in its unexpanded state.

It is also preferred that one or more stop members 64 be formed at or in proximity to proximal end 66 of the shield 26 to limit distal-to-proximal movement of the shield 26 relative to the hub 24. The stop member(s) 64 preferably each have a shoulder 68 arranged generally perpendicularly to the extended surface 45 of the tubular portion 44. In addition, proximal ends of the first inclined surfaces 60 of the flared portions 52 preferably terminate in flat abutment surfaces 70 which are disposed generally perpendicularly to the outer wall 28 of the hub 24. The shoulders 68 and the abutment surfaces 70 are shaped and configured for face-to-face engagement when the shield 26 is in the second position upon proximal-to-distal movement of the shield 26 relative to the hub 24. With the annular portions 52 being nested between the projections 54 and the stop member(s) 64, the shield 26 is locked relative to the hub 24 with movement distally or proximally being hindered. The amount of "free play" of the flared portions 52 in the locked state is a function of the spacing between the upper surfaces 58 of the projections 54 and the shoulders 68 of the stop members 64, and is defined such that distal-to-proximal movement of the shield 26 (locked in the second position) is limited to prevent exposure of the sharpened distal end 40 of needle cannula 36. Advantageously, the engagement surfaces 25 may be defined on the stop members 64.

Optionally, one or more detents 72 may be provided to extend inwardly from the tubular portion 44 at locations intermediate the projections 54 and the stop members 64. The detents 72 reduce the diameter of the tubular portion 44 and interferingly engage the flared portions 52 to generate holding force between the hub 24 and shield 26 to further limit movement of the shield 26 out of the second position. Inclined surfaces 74 may be provided to facilitate the contraction of the flared portions 52 in engaging the detents 72.

Figure 5:
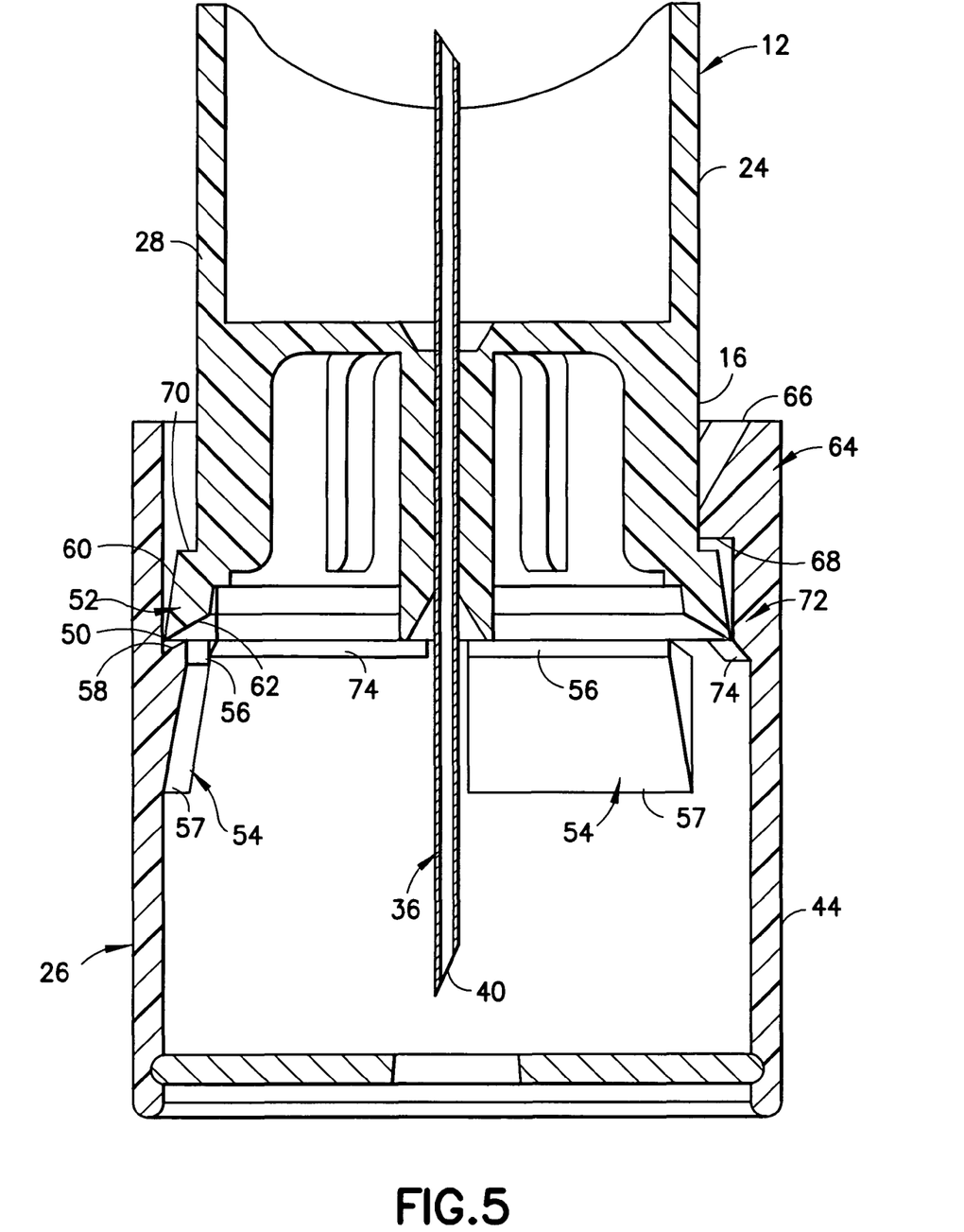
FIG. 5 is a cross-sectional view of a medication pen having a needle cannula affixed directly thereto.

In a second embodiment of the invention, as show in FIG. 5, the needle cannula 36 may be directly affixed to the distal end 16 of the pen body 12. The hub 24 is located at the distal end 16 and may be formed unitarily (i.e., as one piece) with, rigidly affixed to, or removably affixed to the pen body 12 about the needle cannula 36. FIG. 5 shows the hub 24 being unitarily formed with the pen body 12. Here, the shield 26 and the exterior of the hub 24 operate and are formed as described above.

As will be appreciated by those skilled in the art, the shield 26 is formed with sufficient length to enclose the distal end 40 of the needle cannula 36 and prevent inadvertent contact therewith when the shield 26 is in the second position. Advantageously, with the described structure, the needle assembly 14 may be removed from the pen body 12 with the shield 26 being maintained in an extended position (i.e., the second position). Moreover, the cap 20 can be formed to mount onto the needle assembly 14 after use to cover the proximal end 42 of the needle cannula. Alternatively, the locked needle assembly 14 in an extended position can be disposed of with the pen body 12, if, for example, the needle assembly 14 is non-removably affixed to the pen body 12.

To facilitate threaded removal and mounting of the needle assembly 14 relative to the pen body 12, complementary ribs and grooves may be provided to extend longitudinally along the hub 24 and the shield 26 to prevent relative rotation therebetween as disclosed in U.S. Published patent application Ser. No. 2002/0133122 A1. By preventing relative rotation between the hub 24 and the shield 26, the shield 26 can be easily grasped in mounting or dismounting the needle assembly 14 from the pen body 12. If no rotational fixing is provided, the hub 24 has to be grasped in mounting or dismounting the needle assembly 14.

While the invention has been described in relation to the preferred embodiments with several examples, it will be understood by those skilled in the art that various changes may be made without deviating from the spirit and scope of the invention as defined in the appended claims.

What is claimed is:

1. A medication delivery pen assembly comprising:
a pen body adapted to receive a medicinal container inside the pen body; and
a needle assembly having a hub mounted to the pen body;
the hub comprising a cavity defined by a wall having an interior surface with features defined thereon for mounting the pen body,
the hub further comprising,
a needle mounting member, and transverse webbing connecting the wall and the needle mounting member,
a needle cannula extending through said hub and rigidly mounted to the mounting member on the hub, having a distal end sharpened for insertion into a patient and a proximal end adapted for insertion into a medicinal container, the needle cannula defining a central axis of the hub, and
a shield having a tubular portion telescopingly disposed about at least a portion of said hub, said tubular portion having an internal surface and having a first projection extending inwardly from said internal surface toward the central axis, said first projection having a first inclined engagement surface that faces distally and inwardly toward the central axis and a second inclined engagement surface that faces proximally and outwardly from the central axis, said hub having an annular second projection flaring outwardly from the central axis at the distal end of the hub, said second projection including a first inclined surface that faces proximally and outwardly from the central axis and a second inclined surface that faces distally and inwardly toward the central axis, such that said first and second inclined surfaces converge at the distal end of the hub to create said flaring second projection;
complementary ribs and grooves extending longitudinally along the hub and the shield preventing relative rotation between the hub and the shield;
wherein said shield is axially displaceable along said hub distally from a first position, where the shield is releasably held against the hub in an interference fit, and where said distal end of said needle cannula is exposed, to a locked and extended second position, where said distal end of said needle cannula is enclosed by said shield, and wherein, upon said shield being displaced to said second position, a portion of the first inclined surface of said second projection resiliently presses against and is deflectibly urged past a portion of the first inclined engagement surface of said first projection into an expanded state so that distal-to-proximal movement of said shield relative to said hub is hindered by interengagement of a portion of the second inclined surface of said second projection and a portion of the second inclined engagement surface of said first projection.

2. An assembly as in claim 1, further comprising at least one stop member extending inwardly of said shield toward the central axis and formed to engage said hub and limit distal movement of said shield relative to said hub upon expansion of the second projection.

3. An assembly as in claim 2, wherein said at least one stop member is proximally spaced from said first projection.

4. An assembly as in claim 1, wherein said hub of said needle assembly is removably mounted to said pen body.

5. An assembly as in claim 4, wherein said needle assembly and said pen body are formed with cooperating thread members to allow for threaded mounting of said hub on said pen body.

6. An assembly as in claim 1, wherein said cannula includes a proximal end sharpened for insertion into a septum of a medicinal container disposed in said pen body.

7. An assembly as in claim 1, wherein a plurality of said first projections are provided circumferentially spaced-apart on said internal surface of said shield.

8. A needle assembly comprising
a hub having a cavity defined by having an interior surface with features defined thereon for mounting on a pen body, a needle mounting member, and transverse webbing connecting the wall and the needle mounting member,
a needle cannula extending through said hub and rigidly affixed to the mounting member on the hub, having a distal end sharpened for insertion into a patient and a proximal end adapted for insertion into a medicinal container, the needle cannula defining a central axis of the hub;
a shield having a tubular portion telescopingly disposed about at least a portion of said hub, said tubular portion having an internal surface and having a first projection extending inwardly toward the central axis from said internal surface, said first projection having a first inclined engagement surface that faces distally and inwardly toward the central axis and a second inclined engagement surface that faces proximally and outwardly from the central axis, said hub having an annular second projection flaring outwardly from the central axis at the distal end of the hub, said second projection including a first inclined surface that faces proximally and outwardly from the central axis and a second inclined surface that faces distally and inwardly toward the central axis, such that said first and second inclined surfaces converge at the distal end of the hub to create said flaring second projection
wherein said shield is axially displaceable along said hub distally from a first position, where the shield is releasably held against the hub in an interference fit, and where said distal end of said needle cannula is exposed, to a second locked and extended position, where said distal end of said needle cannula is enclosed by said shield,
wherein, upon said shield being displaced to said second position, a portion of the first inclined surface of said second projection resiliently presses against and is deflectibly urged past a portion of the first inclined engagement surface of said first projection into an expanded state so that distal-to-proximal movement of said shield relative to said hub is hindered by interengagement of a portion of the second inclined surface of said second projection and a portion of the second inclined engagement surface of said first; and
a stop member extending inwardly of said shield toward the central axis and having a surface engaging the hub and limiting distal-to-proximal movement of the shield upon expansion of the second projection.

9. An assembly as in claim 8, wherein said at least one stop member is proximally spaced from said first projection.

10. An assembly as in claim 8, wherein said cannula includes a proximal end sharpened for insertion into a septum of a medicinal container.

11. An assembly as in claim 8, wherein a plurality of said first projections are provided circumferentially spaced-apart on said internal surface of said shield.

12. An assembly as in claim 8, wherein said shield includes a cover located in proximity to an end of said tubular portion, said cover having an aperture formed therein which allows for the passage therethrough of said needle cannula.

13. An assembly as in claim 8, wherein said hub is mountable to a medication delivery pen.

14. A medication delivery pen assembly comprising:
a pen body having a hub having a needle cannula mounted thereon, said needle cannula having a distal end sharpened for insertion into a patient and a proximal end adapted for insertion into a medicinal container, the needle cannula defining a central axis of the hub;
said hub comprising a cavity defined by a wall having an interior surface with features defined thereon for mounting on the pen body, a needle mounting member, and transverse webbing connecting the wall and the needle mounting member; and
a shield having a tubular portion telescopingly disposed about at least a portion of said hub, said tubular portion having an internal surface and having a first projection extending inwardly toward the central axis from said internal surface, said first projection having a first inclined engagement surface that faces distally and inwardly toward the central axis and a second inclined engagement surface that faces proximally and outwardly from the central axis, said hub having an annular second projection flaring outwardly from the central axis at the distal end of the hub, said second projection including a first inclined surface that faces proximally and outwardly from the central axis and a second inclined surface that faces distally and inwardly toward the central axis, such that said first and second inclined surfaces converge at the distal end of the hub to create said flaring second projection,
wherein said shield is axially displaceable along said hub distally from a first position, where the shield is releasably held against the hub in an interference fit, and where said distal end of said needle cannula is exposed, to a locked and extended second position, where said distal end of said needle cannula is enclosed by said shield, and
wherein, upon said shield being displaced to said second position, a portion of the first inclined surface of said second projection resiliently presses against and is deflectibly urged past a portion of the first inclined engagement surface of said first projection into an expanded state so that distal-to-proximal movement of said shield relative to said hub is hindered by interengagement of a portion of the second inclined surface of said second projection and a portion of the second inclined engagement surface of said first projection.

15. An assembly as in claim 14, further comprising at least one stop member extending inwardly of said shield toward the central axis and formed to engage said hub and limit distal movement of said shield relative to said hub upon expansion of the second projection.

16. An assembly as in claim 15, wherein said at least one stop member is proximally spaced from said first projection.

17. An assembly as in claim 14, wherein said cannula includes a proximal end sharpened for insertion into a septum of a medicinal container disposed in said pen body.

18. An assembly as in claim 14, wherein a plurality of said first projections are provided circumferentially spaced-apart on said internal surface of said shield.

19. A medication delivery pen assembly comprising:
a pen body; and
a needle assembly having a hub mounted to the pen body;
the hub comprising a cavity defined by a wall having an interior surface with features defined thereon for mounting on the pen body, and further comprising a needle mounting member, and transverse webbing connecting the wall and the needle mounting member;
a needle cannula extending through said hub and rigidly mounted to the mounting member on the hub having a distal end sharpened for insertion into a patient and a proximal end adapted for insertion into a medicinal container, the needle cannula defining a central axis of the hub; and
a shield having a tubular portion telescopingly disposed about at least a portion of said hub, said tubular portion having an internal surface and having a first projection extending inwardly from said internal surface toward the central axis, said first projection having a first inclined engagement surface that faces distally and inwardly toward the central axis and a second inclined engagement surface that faces proximally and outwardly from the central axis, said hub having an annular second projection flaring outwardly from the central axis at the distal end of the hub, said second projection including a first inclined surface that faces proximally and outwardly from the central axis and a second inclined surface that faces distally and inwardly toward the central axis, such that said first and second inclined surfaces converge at the distal end of the hub to create said flaring second projection, wherein said shield is axially displaceable along said hub distally from a first position, where the shield is coextensive with the hub and releasably held against the hub in an interference fit, and where said distal end of said needle cannula is exposed, to a locked and extended second position, where said distal end of said needle cannula is enclosed by said shield, and wherein, upon said shield being displaced to said second position, a portion of the first inclined surface of said second projection resiliently presses against and is deflectibly urged past a portion of the first inclined engagement surface of said first projection into an expanded state so that distal-to-proximal movement of said shield relative to said hub is hindered by interengagement of a portion of the second inclined surface of said second projection and a portion of the second inclined engagement surface of said first projection.

* * * * *